(12) United States Patent
Buros

(10) Patent No.: US 12,138,112 B2
(45) Date of Patent: Nov. 12, 2024

(54) TECHNIQUES FOR DETERMINING FETAL SITUS DURING AN IMAGING PROCEDURE

(71) Applicant: Julie C. Buros, Fredericksburg, VA (US)

(72) Inventor: Julie C. Buros, Fredericksburg, VA (US)

(*) Notice: Subject to any disclaimer, the term of this patent is extended or adjusted under 35 U.S.C. 154(b) by 0 days.

(21) Appl. No.: 17/692,399

(22) Filed: Mar. 11, 2022

(65) Prior Publication Data

US 2022/0192626 A1    Jun. 23, 2022

Related U.S. Application Data

(63) Continuation of application No. PCT/US2020/050350, filed on Sep. 11, 2020.

(60) Provisional application No. 62/898,932, filed on Sep. 11, 2019.

(51) Int. Cl.
*A61B 8/08* (2006.01)
*A61B 8/00* (2006.01)

(52) U.S. Cl.
CPC .......... *A61B 8/0866* (2013.01); *A61B 8/4254* (2013.01); *A61B 8/463* (2013.01); *A61B 8/465* (2013.01)

(58) Field of Classification Search
None
See application file for complete search history.

(56) References Cited

U.S. PATENT DOCUMENTS

| | | |
|---|---|---|
| D370,259 S | 5/1996 | Teich |
| 5,727,949 A | 3/1998 | Bar-Or et al. |
| 5,803,739 A | 9/1998 | Hitchcock |
| D494,626 S | 8/2004 | Taylor |

(Continued)

FOREIGN PATENT DOCUMENTS

| | | |
|---|---|---|
| EM | 0088699860001 | 2/2022 |
| EM | 0088699860007 | 2/2022 |

(Continued)

OTHER PUBLICATIONS

PCT International Search Report and Written Opinion dated Dec. 21, 2020 for International Application No. PCT/US2020/050350, 8 pages.

(Continued)

*Primary Examiner* — Jonathan Cwern
(74) *Attorney, Agent, or Firm* — RMCK Law Group, PLC

(57) ABSTRACT

Techniques for determining fetal situs during an ultrasound imaging procedure are disclosed. The techniques can include obtaining an ultrasound image of a fetus in utero. The fetus will include a torso and a spine and the ultrasound image can comprise a circumferential view of the torso of the fetus. The circumferential view can include at least: (i) an outer border of the torso, and (ii) the spine that includes three landmarks arranged in a triangular orientation. The techniques can further include superimposing a fetal overlay based on an alignment instruction corresponding to an alignment between the outer border of the torso and the three landmarks to obtain an augmented reality image of the fetus. The fetal overlay can include a graphical element indicating a left side and a right side of the fetus. The augmented reality image of the fetus can be output on a display of the ultrasound machine.

20 Claims, 11 Drawing Sheets

(56) References Cited

U.S. PATENT DOCUMENTS

| | | | |
|---|---|---|---|
| D533,904 S | 12/2006 | Ellis | |
| D734,470 S | 7/2015 | Zhang | |
| D755,978 S | 5/2016 | Krause | |
| D844,145 S | 3/2019 | Zhang | |
| 10,368,841 B2 | 8/2019 | Fujiwara et al. | |
| 2005/0245825 A1 | 11/2005 | Krantz et al. | |
| 2014/0228653 A1* | 8/2014 | Kiraly | A61B 8/02 600/382 |
| 2014/0296711 A1 | 10/2014 | Lee | |
| 2016/0133230 A1* | 5/2016 | Daniels | G06F 3/147 345/633 |
| 2016/0170618 A1 | 6/2016 | Song et al. | |
| 2019/0247015 A1* | 8/2019 | Park | A61B 8/5223 |
| 2020/0234435 A1* | 7/2020 | Raynaud | G06T 5/006 |
| 2022/0192626 A1 | 6/2022 | Buros | |

FOREIGN PATENT DOCUMENTS

| | | | |
|---|---|---|---|
| EP | 3435324 A1 | 1/2019 | |
| JP | 2010187987 A | 9/2010 | |
| JP | 2014124269 A | 7/2014 | |
| KR | 20180095464 A | 8/2018 | |

OTHER PUBLICATIONS

Extended European Search Report dated Aug. 28, 2023 for EP Application No. 20863983.1, 8 pages.

Rajiah, P. et al., "Ultrasound of Fetal Cardiac Anomalies," American Journal of Roentgenology, vol. 197, No. 4, Oct. 2011, pp. W747-W760.

Dursun, S. et al., "A novel technique for determining the axis of the fetal heart: Clock position method," Sep. 2020, NIH.gov, https://www.ncbi.nlm.nih.gov/pmc/articles/PMC7495124/#:~:text=Other%20methods%20have%20been%20described,for%20transvaginal%20examination%20was%20used, 2 pages.

Savage, K., "The Lateral Pal," Sep. 2021, YouTube.com, https://www.youtube.com/watch?v=7BQZaoi0J8k, 5 pages.

Spansee, "Midwife Fetal Position Tool," Mar. 2023, amazon.com, https://www.amazon.com/SPANSEE-Position-Supplies-Childbirth-Education/dp/B0BXKY2B1G, 5 pages.

West Kentucky Community & Technical College, Success Stories, Julie Buros, WKCTC Sonography Graduate, Jan. 2023, YouTube.com, https://www.youtube.com/watch?v=MVSoE0pJMwk, 3 pages.

* cited by examiner

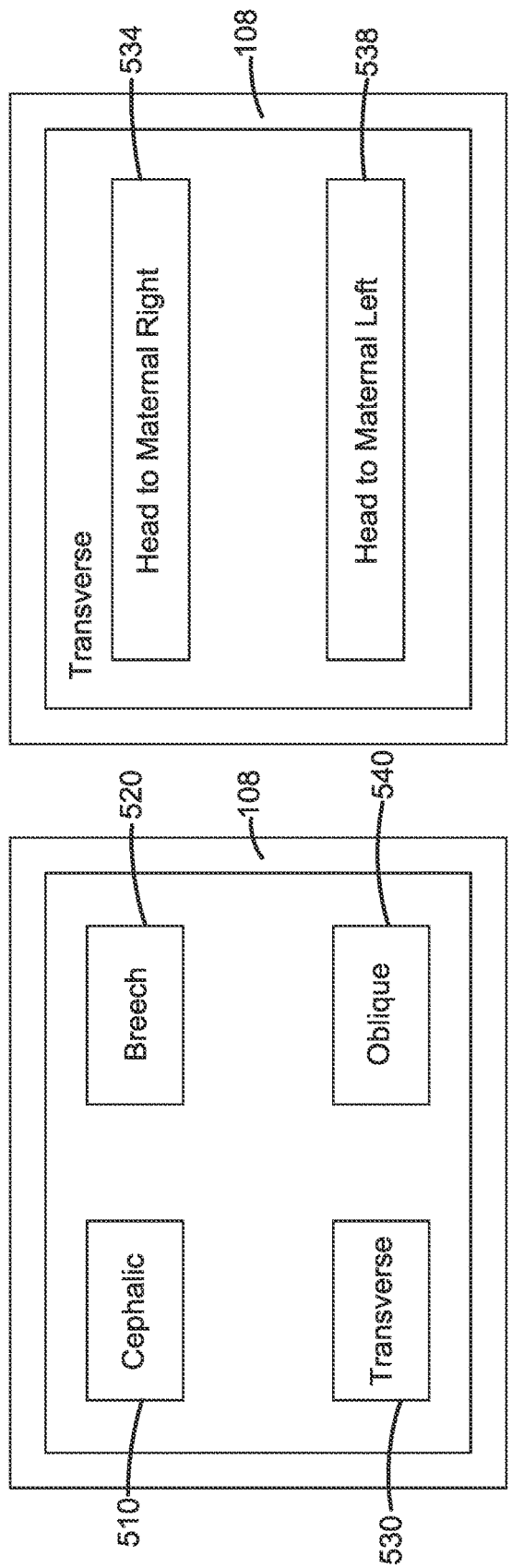
FIG. 5A
FIG. 5B
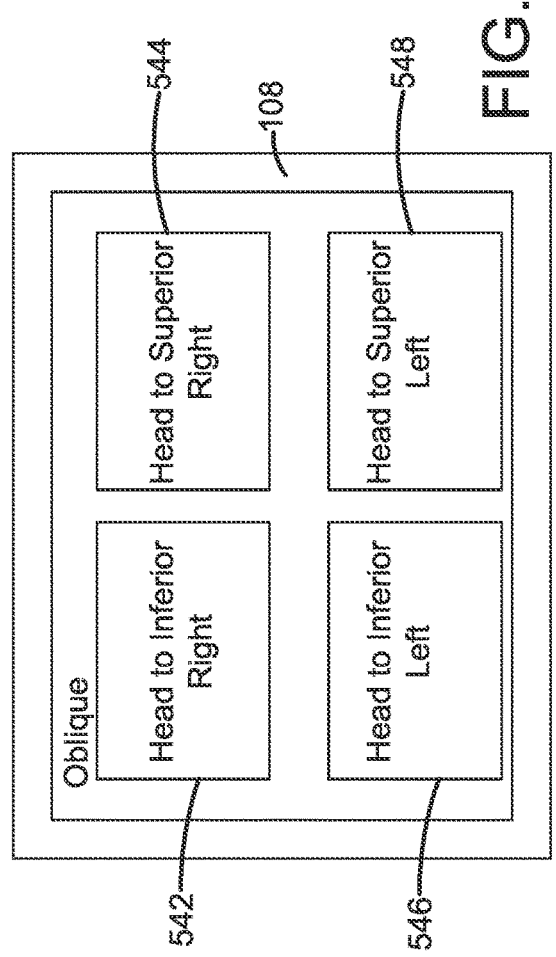
FIG. 5C

TECHNIQUES FOR DETERMINING FETAL SITUS DURING AN IMAGING PROCEDURE

CROSS-REFERENCE TO RELATED APPLICATIONS

This application is a bypass continuation of International Application No. PCT/US2020/050350, filed Sep. 11, 2020, which claims the benefit of U.S. Provisional Application Ser. No. 62/898,932, filed on Sep. 11, 2019. The disclosures of each of the above applications are incorporated herein by reference in their entirety.

FIELD

The present disclosure generally relates to an improved fetal imaging procedure, and more particularly to techniques for easily determining and monitoring fetal situs during an ultrasound imaging procedure of a fetus.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

A fetal ultrasound is an imaging technique that is commonly used during pregnancy to monitor the development of a fetus. Among other things, a typical fetal ultrasound procedure will check the internal organs of the fetus to screen for any abnormalities. For example, fetal ultrasound procedures may screen the fetus for *situs inversus*, a condition in which certain internal organs (heart, stomach, liver, etc.) in the chest/abdomen of the fetus are positioned on the opposite side of their normal positions. In certain situations, a doctor may desire to make special arrangements to assist in the delivery and initial care of a baby that has been diagnosed with *situs inversus* in utero. Accordingly, an ultrasound technologist/sonographer may determine the location of such internal organs during an ultrasound procedure, which is sometimes referred to as "fetal situs."

Current techniques for determining fetal situs during an ultrasound procedure are complex, confusing, and awkward. Experienced sonographers may utilize different techniques for determining fetal situs, and it is not uncommon for two experienced sonographers to disagree on the fetal situs of a particular fetus based on such different techniques. Accordingly, there is a need for improved techniques for determining fetal situs during an ultrasound procedure.

SUMMARY

According to various aspects of the present disclosure, a computer-implemented method for determining fetal situs during an ultrasound imaging procedure is disclosed. The method can include obtaining, at an ultrasound machine having a display and at least one processor, an ultrasound image of a fetus in utero. The fetus will include a torso and a spine and the ultrasound image can comprise a circumferential view of the torso of the fetus. The circumferential view can include at least: (i) an outer border of the torso, and (ii) the spine that includes three landmarks arranged in a triangular orientation. The method can further include superimposing, at the ultrasound machine, a fetal overlay based on an alignment instruction corresponding to an alignment between the outer border of the torso and the three landmarks arranged in the triangular orientation to obtain an augmented reality image of the fetus. The fetal overlay can include a graphical element indicating a left side and a right side of the fetus. The augmented reality image of the fetus can be output on the display of the ultrasound machine.

In some implementations, the alignment instruction can be received at the ultrasound machine via a user input aligning the fetal overlay with the outer border of the torso and the three landmarks arranged in the triangular orientation. In additional or alternative implementations, the alignment instruction can be generated by the ultrasound machine based on the alignment between the outer border of the torso and the three landmarks arranged in the triangular orientation. In such implementations, the method can further include detecting, at the ultrasound machine, movement of the fetus in the ultrasound image, and adjusting, at the ultrasound machine, the fetal overlay based on the movement of the fetus such that the graphical element properly indicates the left side and the right side of the fetus in the augmented reality image of the fetus. The adjusting of the fetal overlay based on the movement of the fetus can be based on the alignment between the outer border of the torso and the three landmarks arranged in the triangular orientation.

In further aspects, the method can further include outputting, on the display of the ultrasound machine, a graphical representation of the fetus, where the graphical representation depicts an orientation of the fetus with respect to the augmented reality image of the fetus. The graphical representation of the fetus can change orientation as a user changes a position of the image.

In some implementations, the method can further include determining, at the ultrasound machine, a neutral position of the augmented reality image of the fetus, and outputting, on the display of the ultrasound machine, a neutral position indicator when the augmented reality image of the fetus is in the neutral position.

In some implementations, the method can further include receiving, at the ultrasound machine, an instruction to change a position of the augmented reality image, and in response to receiving the instruction to change the position, adjusting, at the ultrasound machine, the fetal overlay such that the graphical element properly indicates the left side and the right side of the fetus in the augmented reality image of the fetus. Additionally, in some implementations, the graphical element indicating the left side and a right side of the fetus can comprise at least one translucent color indicator.

In other implementations, the present disclosure is directed to an ultrasound machine that includes a display and at least one processor. The ultrasound machine can perform any, any combination, or all of the above described methods.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 5A-5C is a representation of a display device of the example ultrasound machine of FIG. 2 when displaying various graphical user interfaces during an obstetric ultrasound procedure according to some implementations of the present disclosure;

DETAILED DESCRIPTION

Figure 1:
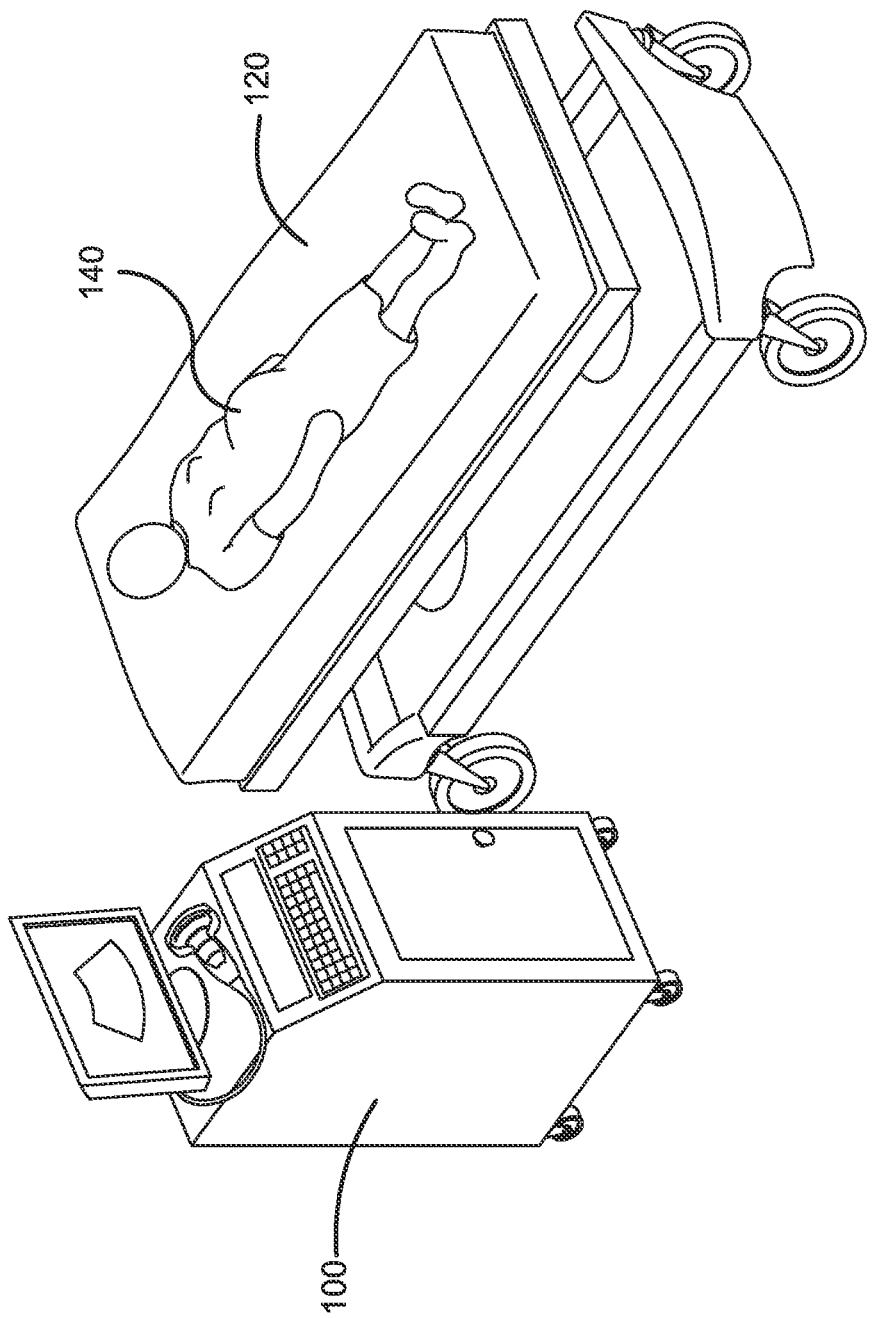
FIG. 1 is an illustration of a typical arrangement of an ultrasound machine and patient utilized for an obstetric ultrasound procedure according to some aspects of the present disclosure.

An ultrasound technologist can capture hundreds of images and videos during an ultrasound procedure. For imaging a patient directly, the ultrasound technologist will have a general understanding of the position of the portion of the patient being imaged based on the position of the ultrasound probe with respect to the patient. For example only, when the ultrasound probe is placed on the right side of the body of the patient, the ultrasound technologist will know or will easily be able to confirm that she/he is imaging the right side of the body. With respect to a fetal ultrasound, however, it may not be easy to determine the portion of the fetus being imaged as the fetus may be oriented in three dimensions within the body of the patient. Further, the fetus may change position during an ultrasound procedure. As described more fully herein, it may be important for an ultrasound technologist to have an understanding of the position and orientation of the fetus within the patient for various aspects of the ultrasound procedure, including but not limited to determining fetal laterality and fetal situs.

As briefly mentioned above, current techniques for determining fetal situs during an ultrasound procedure are complex, confusing, and awkward, and it is not uncommon for errors to be made by even experienced sonographers. Accordingly, the present disclosure is directed to improved techniques for determining fetal situs. More specifically, the present disclosure describes techniques for determining a left side and a right side of a fetus during an imaging procedure and producing an augmented reality image of the fetus that is displayed to the sonographer. The augmented reality image includes a fetal overlay superimposed over the fetal image. The fetal overlay can include a graphical element that indicates the left and right sides of the fetus. In an example implementation, the graphical element may comprise a translucent color indicator that "highlights" and differentiates the different sides of the fetus, such as presenting the left side of the fetus in a green color and the right side of the fetus in a red color. Other implementations of the graphical element are within the scope of the present disclosure.

The fetal overlay is aligned with the fetus in the fetal image based on an alignment instruction. The alignment instruction can correspond to an alignment between two or more landmarks of the fetus. In an example implementation, the torso and the spine of the fetus can be utilized to generate the alignment instruction. For example only, in a circumferential view of a fetus at certain locations, the fetal image includes a view of the outer border of the torso and the spine of the fetus. More specifically, and as further described below, the spine may appear to have three landmarks, circles, or "dots" arranged in the triangular orientation and proximate to the outer border (or back) of the torso. Two of these landmarks will be positioned closer to the outer border of the torso, and the third landmark will be arranged more centrally in the torso. By utilizing these landmarks and the outer border of the torso, the fetal overlay may be aligned to partition the image into two sides, e.g., by extending a line from the outer border of the torso nearest the two landmarks, between the two landmarks closest to the outer border and through the third landmark to the other side of the torso.

While the fetal overlay will partition the fetal image into two sides, as described above, further information may be needed to label the two sides correctly (left side v. right side). Accordingly, in some aspects, the position or presentation of the fetus (head up, head down, head left, head right, etc.) in the fetal image can be utilized as this further information. The presentation of the fetus can be determined in various ways, including but not limited to receiving a user input from the sonographer indicating the head position, capturing a sagittal view of the fetus by the imaging system in order to detect/determine the presentation, or a combination thereof. In this manner, the fetal overlay can indicate the left side and the right side of the fetus in the augmented reality image. Further, the sonographer can obtain further images of the fetus while the augmented reality image is displayed, thereby enabling the sonographer to more easily detect and record fetal situs, and also capture additional images of the organs of the fetus while the sides of the fetus are displayed.

Referring now to FIG. 1, a typical arrangement utilized for an obstetric ultrasound procedure is shown. The arrangement includes an ultrasound machine 100 arranged proximate a bed 120 or other support structure on which a patient 140 can be located. The ultrasound machine 100 is typically arranged on the right side of the patient 140, proximate the patient's head as shown in FIG. 1. Such an arrangement provides an ultrasound technologist with a standard imaging orientation with respect to the patient 140 and her fetus, and permits the ultrasound technologist to properly orient the image of the fetus.

Figure 2:
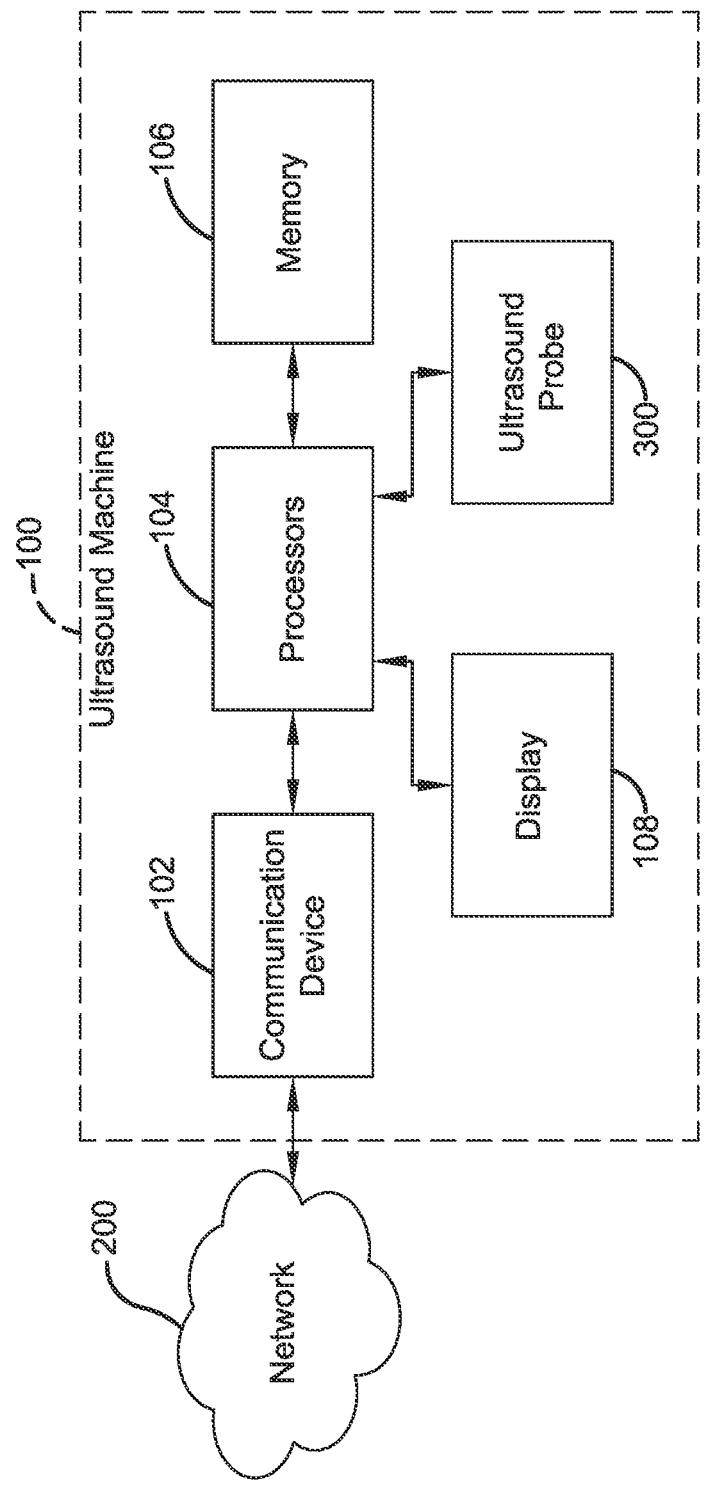
FIG. 2 is a functional block diagram of an example ultrasound machine according to some aspects of the present disclosure.

A functional block diagram of an example ultrasound machine 100 is illustrated in FIG. 2. The ultrasound machine 100 is shown as including a communication device 102, one more processors 104, a memory 106, a display device 108, and an ultrasound probe 300. The processor(s) 104 can control the operation of the ultrasound machine 100, including implementing at least a portion of the techniques of the present disclosure. The term "processor" as used herein is intended to refer to both a single processor and multiple processors operating together, e.g., in a parallel or distributed architecture. The communication device 102 can be configured for communication with other devices (e.g., various server computing devices, peripheral computing elements, or other computing devices) via a network 200 or other communication connection. One non-limiting example of the communication device 102 is a transceiver, although other forms of hardware are within the scope of the present disclosure.

The memory 106 can be any suitable storage medium (flash, hard disk, etc.) configured to store information. For example, the memory 106 may store a set of instructions that are executable by the processor 104, which cause the ultrasound machine 100 to perform operations (e.g., such as the operations of the present disclosure). The display device 108 can display information to the ultrasound technologist and patient 140. In some implementations, the display device 108 can comprise a touch-sensitive display device (such as a capacitive touchscreen and the like), although non-touch display devices are within the scope of the present disclosure. The ultrasound probe 300 is typically a handheld device that outputs sound waves that reflect off of elements of a body. The ultrasound probe 300 further includes a transducer that receives the reflected sound waves and communicates a representation of the sound waves, e.g., to the processor 104, for generating an ultrasound image.

While the techniques of the present disclosure are described herein in the context of the ultrasound machine 100 and associated components of the ultrasound machine 100, it is specifically contemplated that each feature of the techniques may be performed by a single ultrasound machine 100 alone, a plurality of ultrasound machines 100 operating together, one or more server computing devices, peripheral computing elements, or other computing devices operating in coordination with one or more ultrasound machines 100, or any combination thereof.

Figure 3:
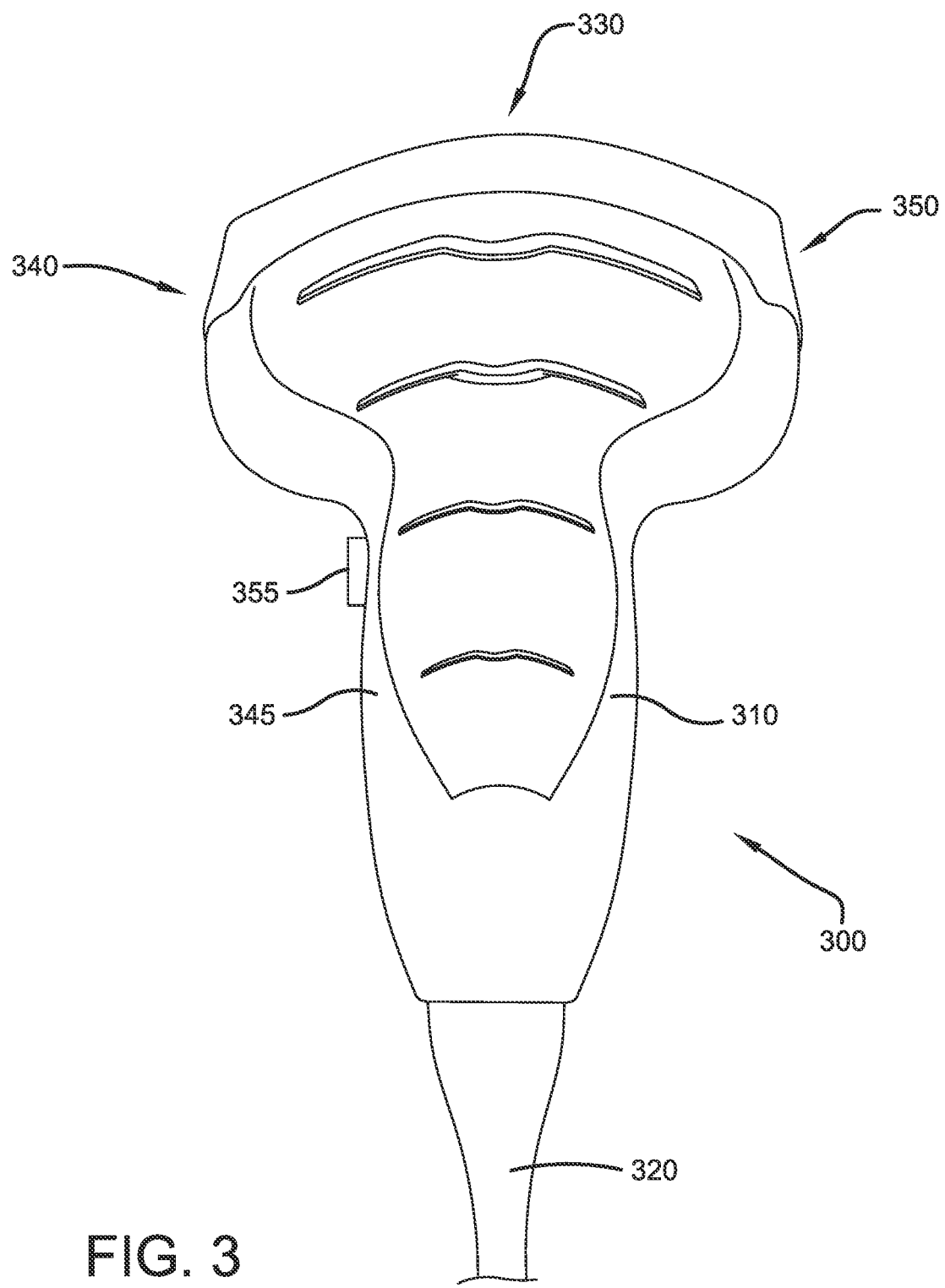
FIG. 3 is an illustration of an example ultrasound probe of the example ultrasound machine of FIG. 2.

With further reference to FIG. 3, an example ultrasound probe 300 is illustrated. The ultrasound probe 300 includes a housing 310 and a connecting wire 320 that couples the ultrasound probe 300 with the other components of the ultrasound machine 100. The ultrasound probe 300 further includes a front portion 330, a left side 340, and a right side 350. The front portion 330 may include a lens or other component suitable for transmitting the sound waves from the ultrasound probe 300 and receiving the reflected sound waves. In order to assist the ultrasound technologist in maintaining the proper orientation of the ultrasound probe 300, a projection, flange, or other mechanical differentiator (referred to herein as "notch 355") can be arranged on one of the sides of a graspable portion 345 of the ultrasound probe, e.g., on the left side 340 as shown in FIG. 3. In some aspects, and as further described below, the ultrasound technologist will align the notch 355 of the ultrasound probe 300 in a specific direction during an ultrasound procedure in order to maintain an appropriate frame of reference for the fetal images generated by the ultrasound machine 100.

Figure 4:
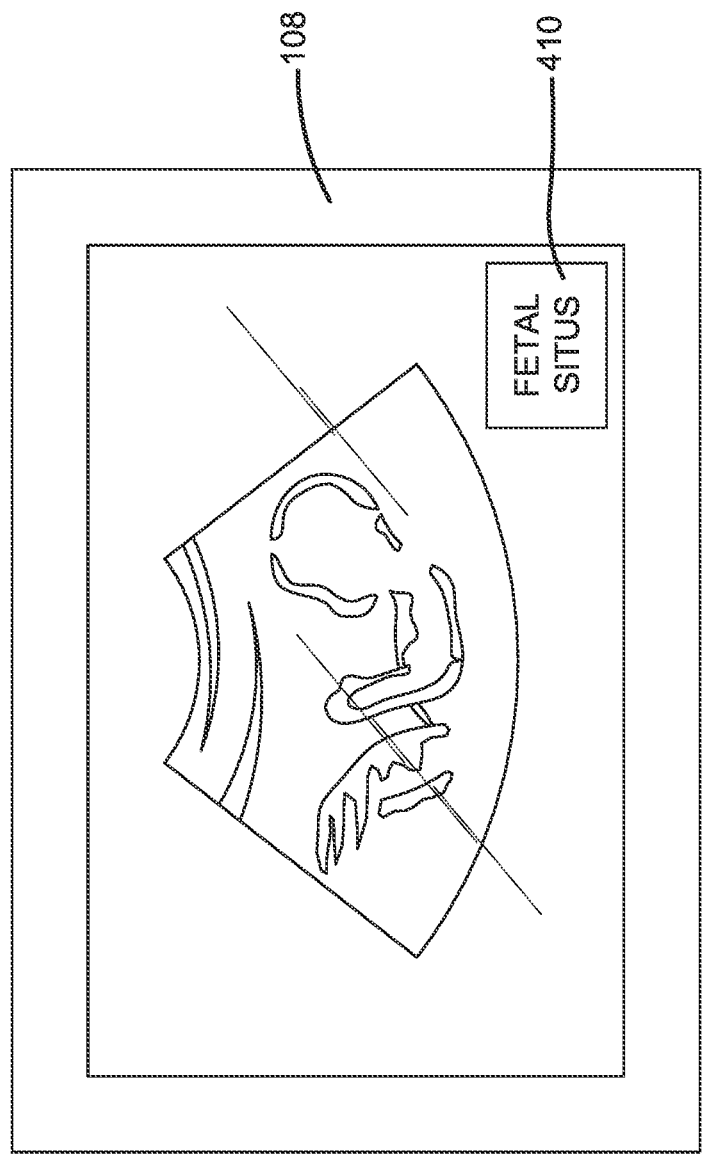
FIG. 4 is a representation of a display device of the example ultrasound machine of FIG. 2 when displaying a graphical user interface during an obstetric ultrasound procedure according to some implementations of the present disclosure.
Figure 5D:
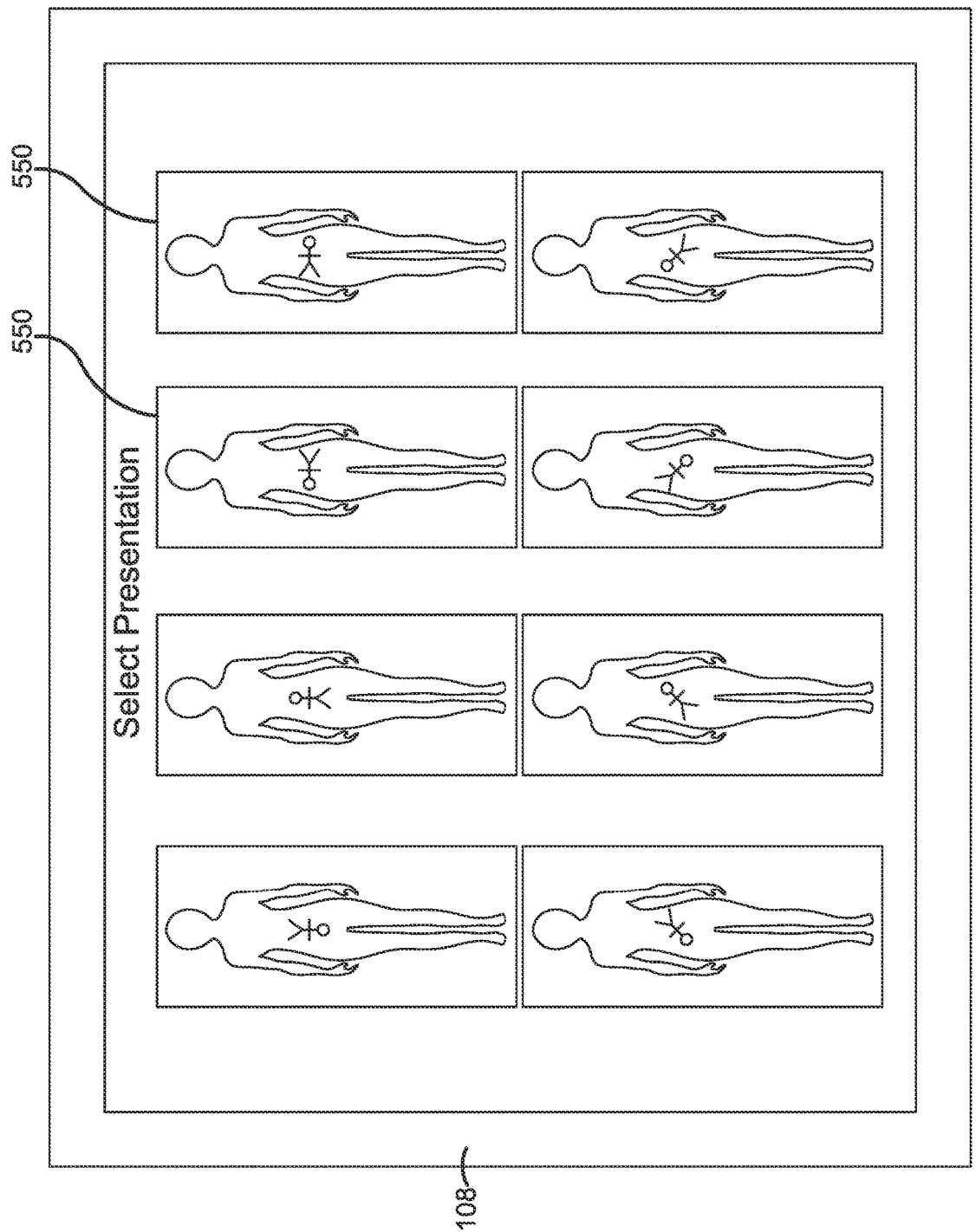
FIG. 5D is a representation of a display device of the example ultrasound machine of FIG. 2 when displaying another graphical user interface during an obstetric ultrasound procedure according to some implementations of the present disclosure.

With further reference to FIGS. 4-10, a technique for determining fetal situs during a fetal ultrasound procedure utilizing the ultrasound machine 100 is disclosed. In some implementations, a fetal situs function of the ultrasound machine 100 can be initiated, e.g., by the ultrasound technologist selecting a button or icon 410 on a user interface 400 displayed by the display device 108 (FIG. 4). In response, the ultrasound machine 100 can operate to determine a fetal position. For example only, the ultrasound machine 100 can query the ultrasound technologist to input a fetal position, such as cephalic, breech, transverse, or oblique, as further described below. Additionally or alternatively, the ultrasound machine 100 may utilize an ultrasound scan to determine the fetal position, e.g., by prompting the ultrasound technologist to utilize the ultrasound probe 300 to capture a particular image, from which the ultrasound machine 100 can determine the fetal position, e.g., via image recognition techniques. Other techniques for determining the fetal position are contemplated by this disclosure As shown in FIG. 5A, the ultrasound machine 100 may query the ultrasound technologist via the display device 108 displaying a user interface 500 including selectable icons for the various fetal positions. When the fetal position is determined to be cephalic 510 or breech 520, the ultrasound machine 100 may accept the fetal position and proceed with the other elements of the technique. When the fetal position is transverse 530 or oblique 540, however, the ultrasound machine 100 may require additional fetal position information. With reference to a transverse fetal position (FIG. 5B), the ultrasound machine 100 may query the ultrasound technologist to select between "Transverse—Head to Maternal Right" 534 or "Transverse—Head to Maternal Left" 538 options on the display 108. With reference to an oblique fetal position 540 (FIG. 5C), the ultrasound machine 100 may query the ultrasound technologist to select between "Oblique—Head to Maternal Inferior Right" 542, "Oblique—Head to Maternal Superior Right" 544, "Oblique—Head to Maternal Inferior Left" 546, and "Oblique—Head to Maternal Superior Left" 548 options on the display 108. Alternatively, and with reference to FIG. 5D, the ultrasound machine 100 can provide graphical elements 550 representative of the various fetal positions for selection by the ultrasound technologist.

Figure 6:
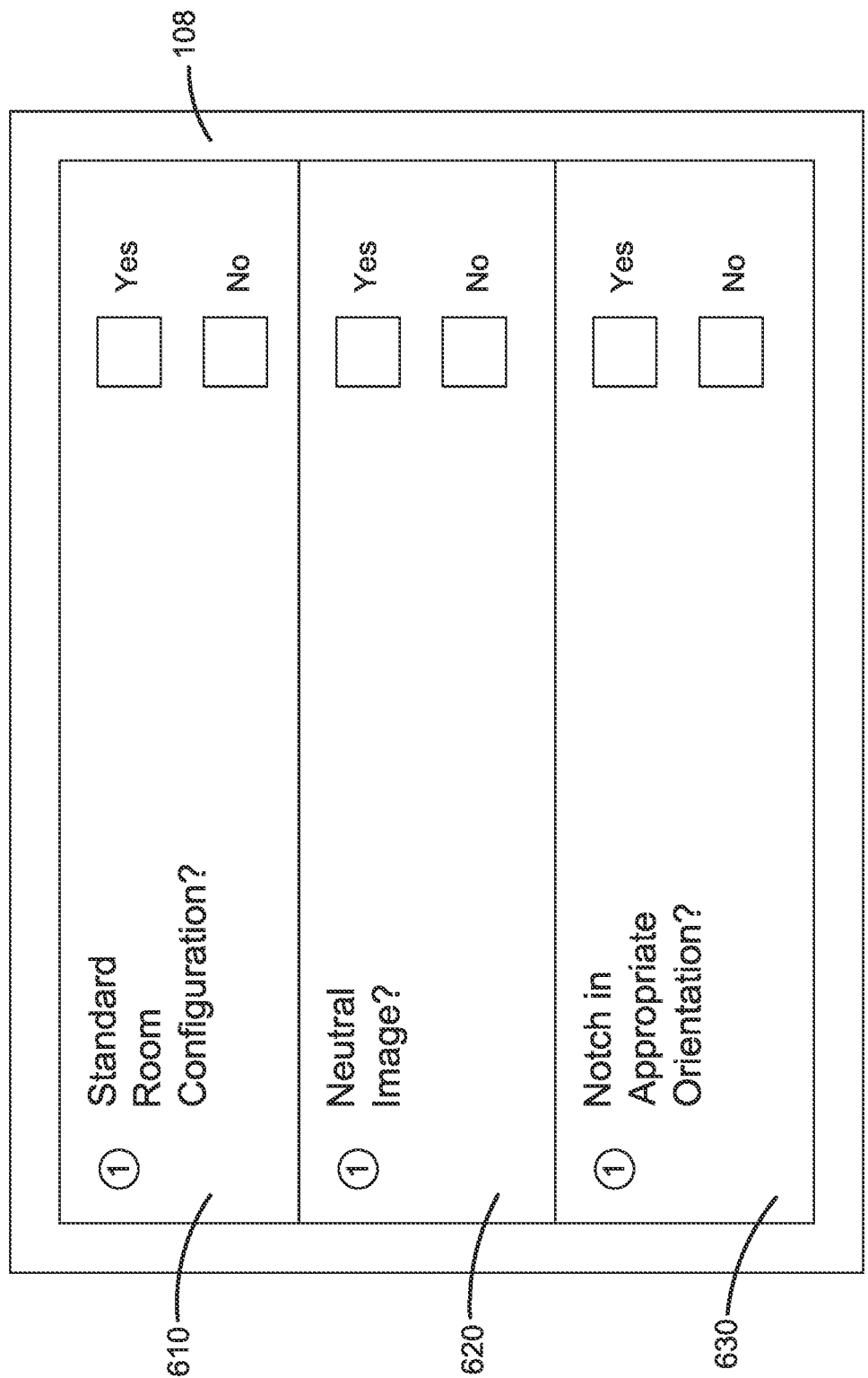
FIG. 6 is a representation of a display device of the example ultrasound machine of FIG. 2 when displaying yet another graphical user interface during an obstetric ultrasound procedure according to some implementations of the present disclosure.

Upon input of the fetal position, and referring now to FIG. 6, the ultrasound machine 100 can determine or obtain further information related to the ultrasound procedure being performed. For example only, the ultrasound machine 100 may query the ultrasound technologist via the display device 108 by displaying a user interface 600. At 610, the ultrasound technologist can be prompted to select or confirm the room configuration. In the illustrated example, the prompt 610 queries the ultrasound technologist to confirm that the standard room configuration (ultrasound machine 100 located on maternal right) is being utilized. At 620, the ultrasound machine 100 can determine that the ultrasound image being displayed corresponds to a "neutral" position, e.g., either automatically or requiring confirmation by the ultrasound technologist. Finally, at 630, the ultrasound machine 100 can prompt the ultrasound technologist to arrange the ultrasound probe 300 in the appropriate orientation. In some aspects, the appropriate orientation is wherein the notch 355 of the ultrasound probe 300 is directed towards maternal right or towards the head of the patient 140. It should be appreciated that there are various ways in which the room configuration, image type, and notch 355 position can be determined, all of which are within the scope of the present disclosure. For example only, the ultrasound machine 100 and/or ultrasound probe 300 can include a position/orientation sensor (e.g., accelerometer or other sensors) that enables for the automatic determination and monitoring of the position, orientation, etc. of the notch 355.

Figure 7:
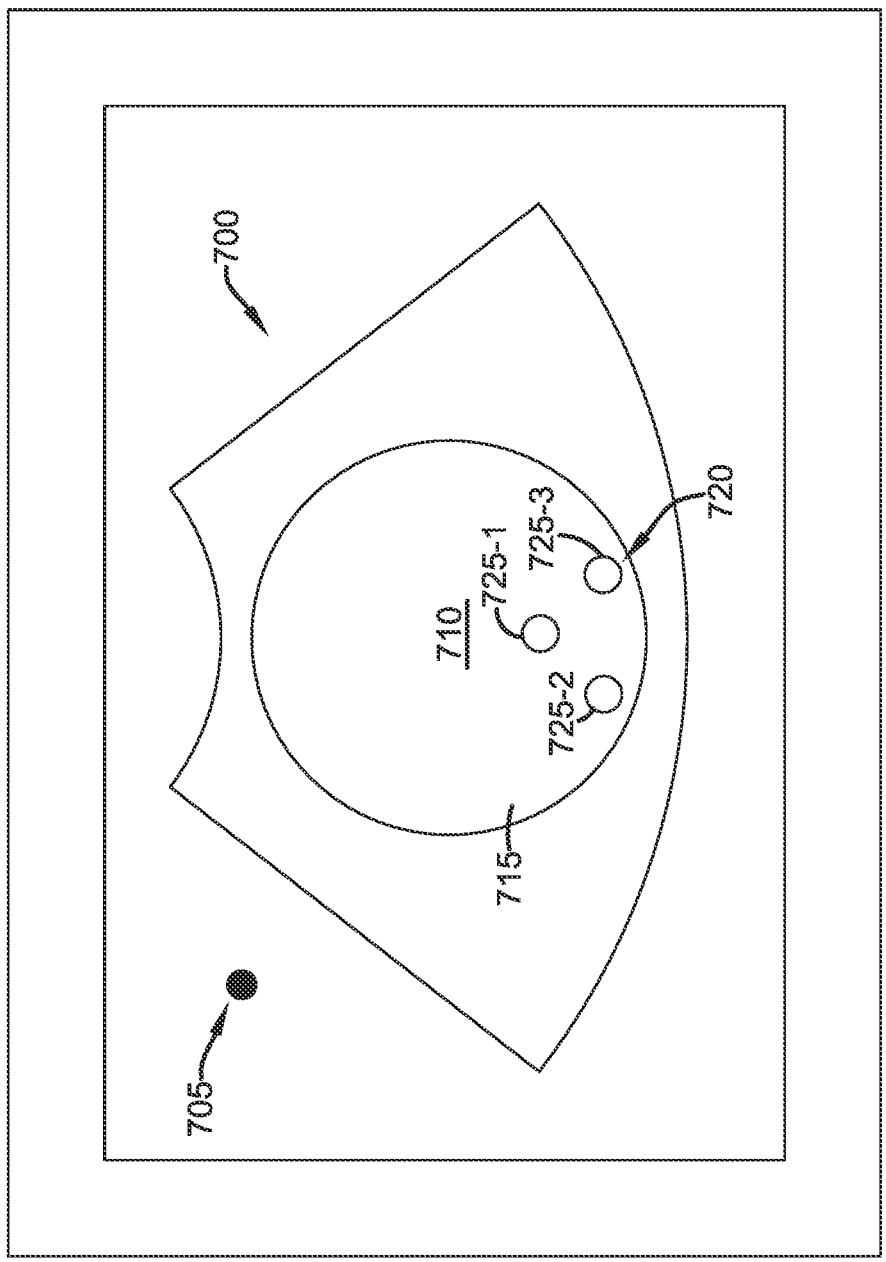
FIG. 7 is a representation of a display device of the example ultrasound machine of FIG. 2 when displaying a further graphical user interface during an obstetric ultrasound procedure according to some implementations of the present disclosure.
Figure 8:
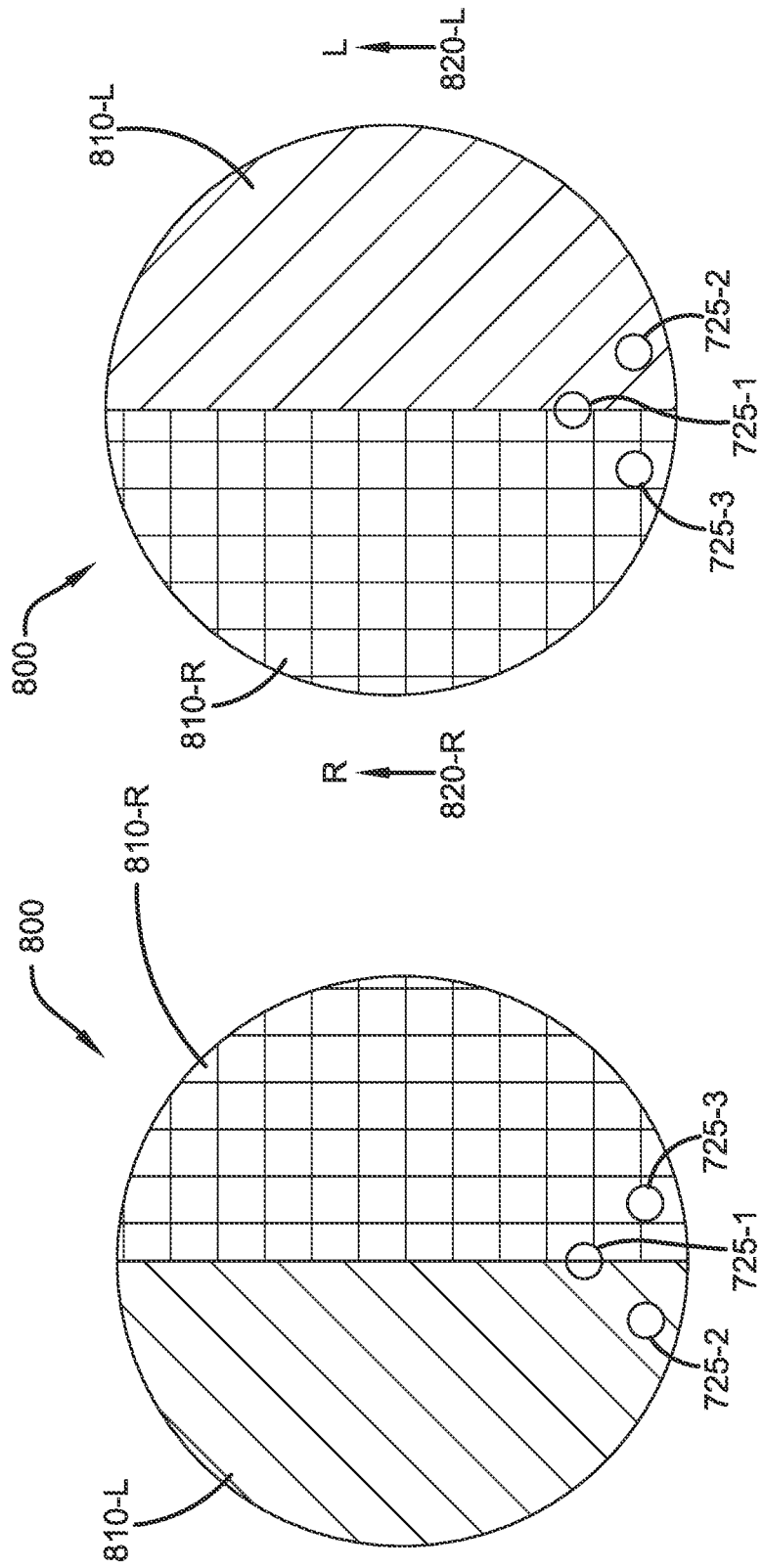
FIGS. 8A and 8B are each an illustration of a fetal overlay to be superimposed over an ultrasound image to obtain an augmented reality image of the fetus according to some implementations of the present disclosure.

Referring now to FIG. 7, when the ultrasound machine 100 determines or otherwise obtains the fetal position information, and the room configuration, neutral image position, and notch 355 orientation are confirmed, the ultrasound machine 100 can instruct the ultrasound technologist to obtain an ultrasound image 700 of a fetus in utero. The ultrasound image 700 can be displayed on the display 108 of the ultrasound machine 100. In some implementations, the display 108 may also display a neutral position indicator 705 so that the ultrasound technologist can easily confirm that the image is in the neutral position during the ultrasound procedure.

The ultrasound image 700 can comprise a circumferential view of the torso 710 of the fetus. Further, the circumferential view can include an outer border 715 of the torso 710 and the spine 720 of the fetus. In some aspects, and as mentioned above, the spine 720 will include three landmarks 725-1, 725-2, and 725-3 arranged in a triangular orientation. As further described below, the ultrasound machine 100 and/or the ultrasound technologist can utilize the orientation of the outer border 715 of the torso and the three landmarks 725-1, 725-2, and 725-3 to determine fetal situs, as further described below.

Figure 9:
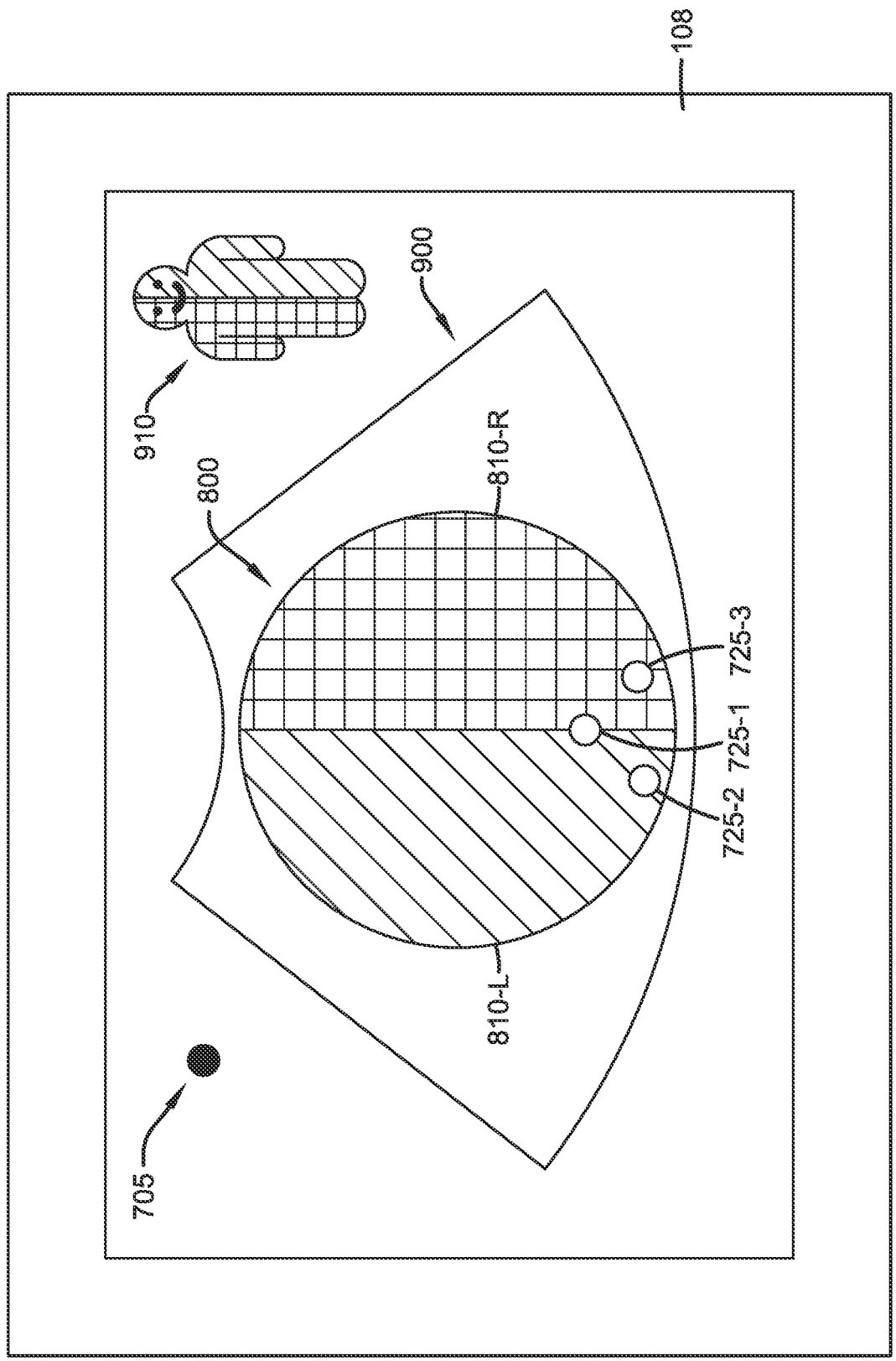
FIG. 9 is a representation of a display device of the example ultrasound machine of FIG. 2 when displaying a particular graphical user interface during an obstetric ultrasound procedure according to some implementations of the present disclosure.

With further reference to FIGS. 8A, 8B and 9, based on the various inputs described above, the ultrasound machine 100 can superimpose a fetal overlay 800 over the ultrasound image 700 to obtain an augmented reality image 900 of the fetus. The fetal overlay 800 can include a graphical element 810, 820 indicating a left side and a right side of the fetus. The graphical element 810, 820 can take the form of any visual indicator that differentiates the fetal left side from the fetal right side in the augmented reality image 900. For example only, in one illustrated example shown in FIG. 8A, the graphical element includes at least one translucent color indicator 810-L or 810-R that bifurcates the torso 710 of the fetus into left (810-L) and right (810-R) sides. In FIG. 8B, the graphical element includes at least one translucent color indicator 810-L or 810-R that bifurcates the torso 710 of the fetus into left (810-L) and right (810-R) sides, and a left (820-L) and right (820-R) side icon ("L" and "R" arranged proximate the appropriate portions of the fetus). Other forms of graphical elements are within the scope of the present disclosure.

As shown in FIGS. 8A and 8B, the fetal overlay 800 can take two forms: the first with the left side on the left side of the overlay when the landmarks 725 are arranged towards the bottom of the frame (FIG. 8A) and the second with the right side on the left side of the overlay when the landmarks 725 are arranged towards the bottom of the frame (FIG. 8B). The determination of which fetal overlay 800 to utilize is based on the fetal position information described above (cephalic 510, breech 520, transverse 530, or oblique 540) when the ultrasound probe 300 is in the proper orientation. For example only, the fetal overlay 800 of FIG. 8A may be appropriate for the cephalic 510 and "Transverse—Head to Maternal Right" 534 positions and the fetal overlay 800 of FIG. 8B can be appropriate for the breech 520 and "Transverse—Head to Maternal Left" 538 positions. Additionally, the fetal overlay 800 of FIG. 8A may be appropriate for the "Oblique—Head to Maternal Inferior Right" 542 and "Oblique—Head to Maternal Inferior Left" 546 positions and the fetal overlay 800 of FIG. 8B can be appropriate for the "Oblique—Head to Maternal Superior Right" 544 and "Oblique—Head to Maternal Superior Left" 548 positions. The above descriptions are dependent upon the proper orientation of the notch 355 with respect to the mother, as described above. In some implementations, the ultrasound machine 100 can provide a prompt, output, or other reminder to the ultrasound technologist to ensure that the notch 355 is properly oriented when the position of the fetus is input.

The ultrasound machine 100 can superimpose the fetal overlay 800 based on an alignment instruction corresponding to an alignment between the outer border 715 of the torso 710 and the three landmarks 725 arranged in the triangular orientation. In some implementations, the alignment instruction can be generated by the ultrasound machine 100 automatically. For example only, the ultrasound machine 100 may utilize an image recognition or other visual matching algorithm on the ultrasound image 700 to detect one or more of the outer border 715 of the torso 710 and the three landmarks 725 to generate an alignment instruction corresponding to the appropriate position of the fetal overlay 800.

Alternatively, the ultrasound machine 100 may receive the alignment instruction via a user input (e.g., from the ultrasound technologist) aligning the fetal overlay 800 in the appropriate position. The user input can take various forms, including but not limited to an input corresponding to the position and rotation of the fetal overlay 800 to align the outer border 715 of the torso 710 and landmarks 725 with corresponding matching landmarks/icons/elements/etc. in the fetal overlay 800. In some aspects, a combination of the computer generated and user input alignment instructions can be utilized, e.g., where the ultrasound machine 100 generates an initial alignment of the fetal overlay 800 and the ultrasound technologist can modify the generated alignment to ensure a desired alignment.

Referring now to FIG. 9, an example augmented reality image 900 of the fetus is shown as output by the display device 108. The illustrated augmented reality image 900 includes the fetal overlay 800 of FIG. 8A in a proper alignment between the outer border 715 of the torso 710 and the three landmarks 725 arranged in the triangular orientation. The illustrated augmented reality image 900 further includes a graphical representation 910 of the fetus in a position corresponding to the imaging position of the augmented reality image 900. The graphical representation 910 can depict an orientation of the fetus with respect to the augmented reality image 900. In this manner, the augmented reality image 900 provides a visual cue to the ultrasound technologist as to the fetal position during the current imaging procedure.

In some aspects, if and when the ultrasound technologist changes the position of the augmented reality image 900 (from neutral position to various rotated views), the graphical representation 910 of the fetus can also change orientation to correspond to how the current image is positioned. Additionally or alternatively, when the ultrasound technologist changes the position of the augmented reality image 900 (e.g., by providing an instruction to the ultrasound machine 100), the ultrasound machine 100 can adjust the fetal overlay 800 such that the graphical element 810, 820 properly indicates the left side and the right side of the fetus in the rotated or otherwise changed augmented reality image 900. This can be performed, e.g., by the ultrasound machine 100 modifying the fetal overlay 800 in the same manner as the ultrasound image 700 is modified.

According to some implementations of the present disclosure, the ultrasound machine 100 can automatically adjust the fetal overlay 800 in response to movement of the fetus in utero. In such implementations, the ultrasound machine 100 can detect movement of the fetus in the ultrasound image 700 by utilizing a motion detection algorithm. For example only, the motion detection algorithm may store the position of various markers in the ultrasound image 700 and determine when the various markers have changed position. Based on the detected change in position, the ultrasound machine 100 can determine a positional change (direction, rotation, amplitude, etc.) of the fetus. Based on the determined positional change, the ultrasound machine 100 can adjust the fetal overlay 800 in a corresponding manner such that the graphical element(s) 810, 820 properly indicates the left side and the right side of the fetus in the augmented reality image 900. In one example, the ultrasound machine 100 may adjust the fetal overlay based on an alignment between the outer border 715 of the torso 710 and the three landmarks 725 arranged in the triangular orientation, as described above.

Figure 10:
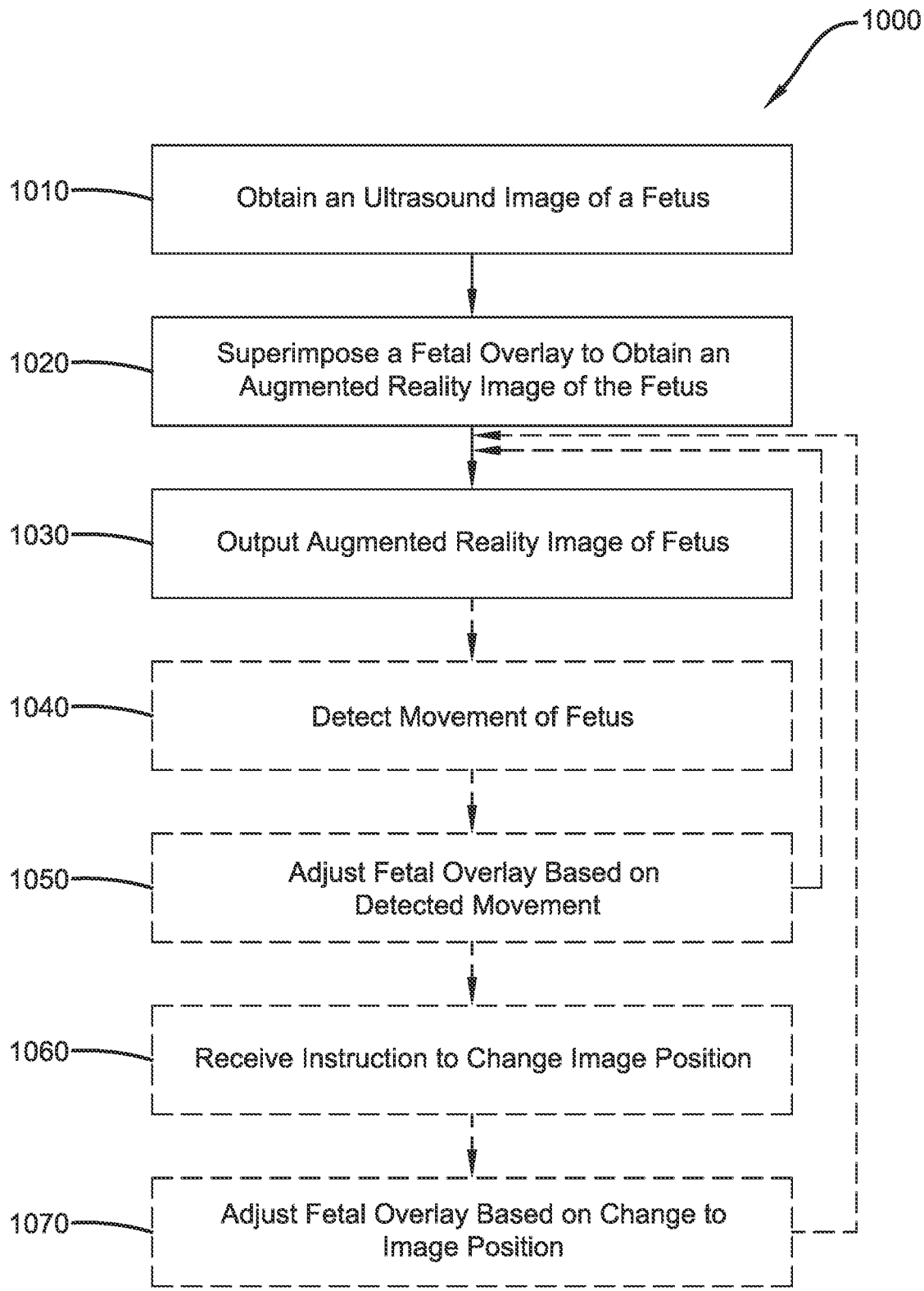
FIG. 10 is a flow diagram of an example technique for determining fetal situs during an imaging procedure according to some implementations of the present disclosure.

Referring now to FIG. 10, an example method 1000 for determining fetal situs during an imaging procedure according to some implementations of the present disclosure is illustrated. For ease of description, the method 1000 will be described as being performed by the ultrasound machine 100 even though, as mentioned above, the method 1000 can be performed by various different devices alone or working cooperatively. At 1010, the ultrasound machine 100 can obtain an ultrasound image 700 of a fetus in utero. In some aspects, the ultrasound image 700 can comprise a circumferential view of the torso 710 of the fetus and an outer border 715 of the torso 710 and (ii) the spine 720 of the fetus. As mentioned above, in certain images, the spine 720 will appears as including three landmarks 725 arranged in a triangular orientation. Based on an alignment instruction corresponding to an alignment of the outer border 715 of the torso 710 and the three landmarks, a fetal overlay 800 can be superimposed over the ultrasound image 700 to obtain an augmented reality image 900. The augmented reality image 900 and the fetal overlay 800 can include a graphical element 810 and/or 820 indicating a left side and a right side of the fetus. The augmented reality image 900 can be output (1030) by the ultrasound device 100.

In some implementations, the method 1000 can further include detecting (1040) movement of the fetus during the ultrasound procedure. In such implementations, the ultrasound machine 100 may also adjust (1050) the fetal overlay 800 based on the movement of the fetus such that the graphical element 810, 820 properly indicates the left side and the right side of the fetus in the augmented reality image 900. Additionally or alternatively, the method 1000 can include receiving (1060) an instruction to change a position of the augmented reality image 900. In response to receiving 1060 the instruction to change the position, the ultrasound machine 100 can automatically adjust the fetal overlay 800 such that the graphical element 810, 820 properly indicates the left side and the right side of the fetus in the augmented reality image 900 as re-positioned.

In addition to the above, the present techniques can be utilized to perform additional functions with respect to the orientation and position of the fetus and its associated body parts. For example only, based on the determination of the left and right side of the fetus described, a cardiac overlay can be generated and superimposed over the heart and/or its various structures. Similar to the fetal overlay described above, the cardiac overlay can include a graphical element that indicates the anatomical left and right sides of the heart, its various structures/components (outflow tracts, branches, confluences, valves, septa, walls, etc.), or a combination thereof. In an example implementation, the graphical element may comprise a translucent color indicator that "highlights" and differentiates the different sides of the heart (which can be referred to as "cardiac laterality"), such as presenting the left side of the heart in a green color and the right side of the heart in a red color. Other implementations of the graphical element are within the scope of the present disclosure.

In another possible implementation, the present techniques can be utilized to assist in the determination of cardiac position and axis. For example only, the fetal overlay 800 can be utilized to automatically generate, and/or assist the ultrasound technologist to position, one of the two "lines" required to determine the angle between the axis of the heart and the thorax centerline. Once generated/positioned, the ultrasound technologist can provide an input indicative of the other "line" and the angle can be automatically determined by the ultrasound machine 100.

The present techniques can provide for further determinations based on the fetal overlay 800. As mentioned above, the fetal overlay 800 can be utilized to display the center axis of the heart ("cardiac axis line"). The ultrasound machine 100 (e.g., in conjunction with assistance from the ultrasound technologist in some aspects) can utilize the cardiac axis line to perform various calculations and determinations. For example only, techniques can include obtaining the circumference of the heart on the left and right sides to calculate the ratio between the left and right sides of the heart. Other ratios can include, e.g., left side circumference to right side circumference/right side circumference to left side circumference, left side circumference to total cardiac circumference, right side circumference to total cardiac circumference, and cardiac circumference to thorax circumference. Various other distances and measurements can be calculated, such as distance between cardiac landmarks (valves, outflow tracts, etc.) and volume/distance ratios.

In some implementations, the fetal overlay 800 and associated graphical element can be extended to not only differentiate the different sides of the heart, but also any associated outflow tracts, such as pulmonary arteries, the aorta, and the like. In this manner, the fetal overlay 800 can assist the ultrasound technologist to visualize the outflow tracts, e.g., to compare the shape of such outflow tracts to the expected shape thereof. Furthermore, the techniques can be utilized to generate additional directional lines of the various outflows to generate angles with other directional lines (such as the cardiac axis line). In some embodiments, the fetal overlay 800 can remain in three/four-dimensional imaging session to confirm appropriate positioning and/or determine any unexpected positioning of cardiac features.

In some further aspects, the present techniques can utilize a landmark or landmarks different from the spinal landmarks/torso described above to assist in the determination of fetal left/right sides. For example only, the arch of a foot of the fetus can be utilized to assist in the left/right side determination. In a fetal position in which the soles of the fetal feet face away from the fetal body and the legs, ankles, feet, etc. are anatomically "normal," the arches of the feet can provide an indication of the left and right sides of the fetus. For example only, in the cephalic fetal position, the arch of the left foot will appear to have a "C" shape and the right foot will have a backwards "C" shape in a neutral image (when the heel is down or in the lower/posterior part of the ultrasound image). Accordingly, a fetal overlay 800 can align and utilize the "C" shape of the arch to align and distinguish between the left and right sides of the fetus. Other implementations of landmarks are within the scope of the present disclosure.

It should be appreciated that the various techniques of the present disclosure can be utilized in conjunction to confirm the determination of fetal left/right sides. For example only, the spinal landmarks/torso techniques can be utilized to determine fetal left/right sides, and the arch of a foot of the fetus can be utilized to confirm this determination (or vice versa). Furthermore, the fetal overlay 800 can be extended to not only display the left/right side of the thorax/heart/etc. of the fetus, but also any appendages that are present during a three/four-dimensional imaging session.

Although the present disclosure is described primarily in the context of an ultrasound procedure, it should be appreciated that the techniques described herein are equally applicable to any imaging technique, mutatis *mutandis*, that can be utilized for imaging of a fetus. Such techniques can include but are not necessarily limited to ultrasound imaging, magnetic resonance imaging (MRI), computed tomography (CT) scanning, and X-ray imaging.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known procedures, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

As used herein, the term "computing device" or processor may refer to, be part of, or include: an Application Specific Integrated Circuit (ASIC); an electronic circuit; a combinational logic circuit; a field programmable gate array (FPGA); a processor or a distributed network of processors (shared, dedicated, or grouped) and storage in networked clusters or datacenters that executes code or a process; other suitable components that provide the described functionality; or a combination of some or all of the above, such as in a system-on-chip. The term computing device may also include memory (shared, dedicated, or grouped) that stores code executed by the one or more processors.

The term code, as used above, may include software, firmware, byte-code and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein, and any references to specific languages are provided for disclosure of enablement and best mode of the present invention.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for determining fetal situs during an ultrasound imaging procedure, comprising:
    obtaining, at an ultrasound machine having a display and at least one processor, an ultrasound image of a fetus in utero, the fetus including a torso and a spine, wherein the ultrasound image comprises a circumferential view of the torso of the fetus, and the circumferential view includes at least: (i) an outer border of the torso, and (ii) the spine that includes three landmarks arranged in a triangular orientation;
    superimposing, at the ultrasound machine, a fetal overlay based on an alignment instruction corresponding to an alignment between the outer border of the torso and the three landmarks arranged in the triangular orientation to obtain an augmented reality image of the fetus, the fetal overlay including a graphical element indicating a left side and a right side of the fetus; and
    outputting, on the display of the ultrasound machine, the augmented reality image of the fetus.

2. The computer-implemented method of claim 1, wherein the alignment instruction is received at the ultrasound machine via a user input aligning the fetal overlay with the outer border of the torso and the three landmarks arranged in the triangular orientation.

3. The computer-implemented method of claim 1, wherein the alignment instruction is generated by the ultrasound machine based on the alignment between the outer border of the torso and the three landmarks arranged in the triangular orientation.

4. The computer-implemented method of claim 3, further comprising:
    detecting, at the ultrasound machine, movement of the fetus in the ultrasound image; and
    adjusting, at the ultrasound machine, the fetal overlay based on the movement of the fetus such that the graphical element properly indicates the left side and the right side of the fetus in the augmented reality image of the fetus.

5. The computer-implemented method of claim 4, wherein the adjusting of the fetal overlay based on the movement of the fetus is based on the alignment between the outer border of the torso and the three landmarks arranged in the triangular orientation.

6. The computer-implemented method of claim 1, further comprising:
    outputting, on the display of the ultrasound machine, a graphical representation of the fetus, the graphical representation depicting an orientation of the fetus with respect to the augmented reality image of the fetus.

7. The computer-implemented method of claim 6, wherein the graphical representation of the fetus changes orientation as a user changes a position of the image.

8. The computer-implemented method of claim 1, further comprising:
    determining, at the ultrasound machine, a neutral position of the augmented reality image of the fetus; and
    outputting, on the display of the ultrasound machine, a neutral position indicator when the augmented reality image of the fetus is in the neutral position.

9. The computer-implemented method of claim 1, further comprising:
    receiving, at the ultrasound machine, an instruction to change a position of the augmented reality image; and
    in response to receiving the instruction to change the position, adjusting, at the ultrasound machine, the fetal overlay such that the graphical element properly indicates the left side and the right side of the fetus in the augmented reality image of the fetus.

10. The computer-implemented method of claim 1, wherein the graphical element indicating the left side and a right side of the fetus comprises at least one translucent color indicator.

11. An ultrasound machine for determining fetal situs during an ultrasound imaging procedure, comprising:
    a display;
    one or more processors; and
    a non-transitory computer-readable storage medium having a plurality of instructions stored thereon, which, when executed by the one or more processors, cause the one or more processors to perform operations comprising:
        obtaining an ultrasound image of a fetus in utero, the fetus including a torso and a spine, wherein the ultrasound image comprises a circumferential view of the torso of the fetus, and the circumferential view includes at least: (i) an outer border of the torso, and (ii) the spine that includes three landmarks arranged in a triangular orientation;

superimposing a fetal overlay based on an alignment instruction corresponding to an alignment between the outer border of the torso and the three landmarks arranged in the triangular orientation to obtain an augmented reality image of the fetus, the fetal overlay including a graphical element indicating a left side and a right side of the fetus; and outputting, on the display, the augmented reality image of the fetus.

12. The ultrasound machine of claim 11, wherein the alignment instruction is received at the ultrasound machine via a user input aligning the fetal overlay with the outer border of the torso and the three landmarks arranged in the triangular orientation.

13. The ultrasound machine of claim 11, wherein the alignment instruction is generated by the ultrasound machine based on the alignment between the outer border of the torso and the three landmarks arranged in the triangular orientation.

14. The ultrasound machine of claim 13, wherein the operations further comprise:

detecting movement of the fetus in the ultrasound image; and adjusting the fetal overlay based on the movement of the fetus such that the graphical element properly indicates the left side and the right side of the fetus in the augmented reality image of the fetus.

15. The ultrasound machine of claim 14, wherein the adjusting of the fetal overlay based on the movement of the fetus is based on the alignment between the outer border of the torso and the three landmarks arranged in the triangular orientation.

16. The ultrasound machine of claim 11, wherein the operations further comprise:

outputting, on the display, a graphical representation of the fetus, the graphical representation depicting an orientation of the fetus with respect to the augmented reality image of the fetus.

17. The ultrasound machine of claim 16, wherein the graphical representation of the fetus changes orientation as a user changes a position of the image.

18. The ultrasound machine of claim 11, wherein the operations further comprise:

determining a neutral position of the augmented reality image of the fetus; and outputting, on the display, a neutral position indicator when the augmented reality image of the fetus is in the neutral position.

19. The ultrasound machine of claim 11, wherein the operations further comprise:

receiving an instruction to change a position of the augmented reality image; and in response to receiving the instruction to change the position, adjusting the fetal overlay such that the graphical element properly indicates the left side and the right side of the fetus in the augmented reality image of the fetus.

20. The ultrasound machine of claim 11, wherein the graphical element indicating the left side and a right side of the fetus comprises at least one translucent color indicator.

* * * * *